(12) United States Patent
Stiger et al.

(10) Patent No.: US 6,589,274 B2
(45) Date of Patent: Jul. 8, 2003

(54) STENT DELIVERY CATHETER AND METHOD OF MAKING SAME

(75) Inventors: Mark L. Stiger, Santa Rosa, CA (US); Michael A. Mohn, Santa Rosa, CA (US); Mark Hoekwater, Santa Rosa, CA (US); Lior Sobe, Raanana (IL)

(73) Assignee: Medtronic AVE, Inc., Santa Rosa, CA (US)

( * ) Notice: Subject to any disclaimer, the term of this patent is extended or adjusted under 35 U.S.C. 154(b) by 117 days.

(21) Appl. No.: 09/816,795

(22) Filed: Mar. 23, 2001

(65) Prior Publication Data

US 2002/0138128 A1 Sep. 26, 2002

(Under 37 CFR 1.47)

(51) Int. Cl.[7] .......................... A61F 2/06; A61M 29/00
(52) U.S. Cl. ................. 623/1.11; 623/1.12; 606/192; 606/194
(58) Field of Search .................... 606/192, 194, 606/198, 108; 604/96.01; 623/1.11, 1.12

(56) References Cited

U.S. PATENT DOCUMENTS

| 4,732,152 | A | | 3/1988 | Wallsten |
|---|---|---|---|---|
| 4,950,227 | A | | 8/1990 | Savin et al. |
| 5,078,727 | A | | 1/1992 | Hannam et al. |
| 5,108,416 | A | | 4/1992 | Ryan et al. |
| 5,116,318 | A | | 5/1992 | Hillstead |
| 5,334,153 | A | | 8/1994 | McIntyre et al. |
| 5,403,341 | A | | 4/1995 | Solar |
| 5,409,495 | A | | 4/1995 | Osborn |
| 5,425,710 | A | | 6/1995 | Khair et al. |
| 5,445,646 | A | | 8/1995 | Euteneuer et al. |
| 5,549,635 | A | | 8/1996 | Solar |
| 5,571,135 | A | | 11/1996 | Fraser et al. |
| 5,643,278 | A | | 7/1997 | Wijay |
| 5,662,703 | A | | 9/1997 | Yurek et al. |
| 5,741,326 | A | | 4/1998 | Solovay |
| 5,766,201 | A | | 6/1998 | Ravenscroft et al. |
| 5,776,141 | A | * | 7/1998 | Klein et al. ............. 623/1.11 |
| 5,795,325 | A | | 8/1998 | Valley et al. |
| 5,807,398 | A | | 9/1998 | Shaknovich |
| 5,810,871 | A | | 9/1998 | Tuckey et al. |
| 5,817,100 | A | | 10/1998 | Igaki |
| 5,843,027 | A | | 12/1998 | Stone et al. |
| 5,935,135 | A | | 8/1999 | Bramfitt et al. |
| 5,944,726 | A | | 8/1999 | Blaeser et al. |
| 5,951,569 | A | | 9/1999 | Tuckey et al. |
| 5,964,730 | A | | 10/1999 | Williams et al. |
| 5,972,015 | A | * | 10/1999 | Scribner et al. ............ 606/192 |
| 5,976,155 | A | | 11/1999 | Foreman et al. |
| 5,980,530 | A | | 11/1999 | Willard |
| 6,045,568 | A | * | 4/2000 | Igaki et al. ............ 623/1.11 |
| 6,048,356 | A | | 4/2000 | Ravenscroft et al. |
| 6,056,906 | A | | 5/2000 | Werneth et al. |
| 6,063,112 | A | | 5/2000 | Sgro |
| 6,068,634 | A | * | 5/2000 | Lorentzen Cornelius et al. ......... 623/1.11 |
| 6,110,180 | A | | 8/2000 | Foreman et al. |
| 6,123,712 | A | * | 9/2000 | Di Caprio et al. ......... 606/108 |
| 6,174,316 | B1 | | 1/2001 | Tuckey et al. |
| 6,183,505 | B1 | * | 2/2001 | Mohn, Jr. et al. ......... 623/1.11 |
| 6,280,412 | B1 | * | 8/2001 | Pederson, Jr. et al. .. 604/103.07 |

FOREIGN PATENT DOCUMENTS

| EP | 0 553 960 A1 | 8/1993 |
|---|---|---|
| EP | 0 990 427 A2 | 5/2000 |

* cited by examiner

Primary Examiner—Rodney M. Lindsey

(57) ABSTRACT

A stent delivery catheter includes an extendable shaft portion, a tubular balloon mounted thereon, a stent and a pair of elastic retaining caps. The balloon is mounted onto the catheter at a mounted length that is shorter than the formed length of the balloon to generate excess balloon material which is gathered into circumferential folds. The extendable portion of the catheter shaft elongates in response to tension applied by the balloon as the folds open during inflation. Elongation of the catheter shaft drives the retaining caps apart to uncover the ends of the stent.

17 Claims, 4 Drawing Sheets

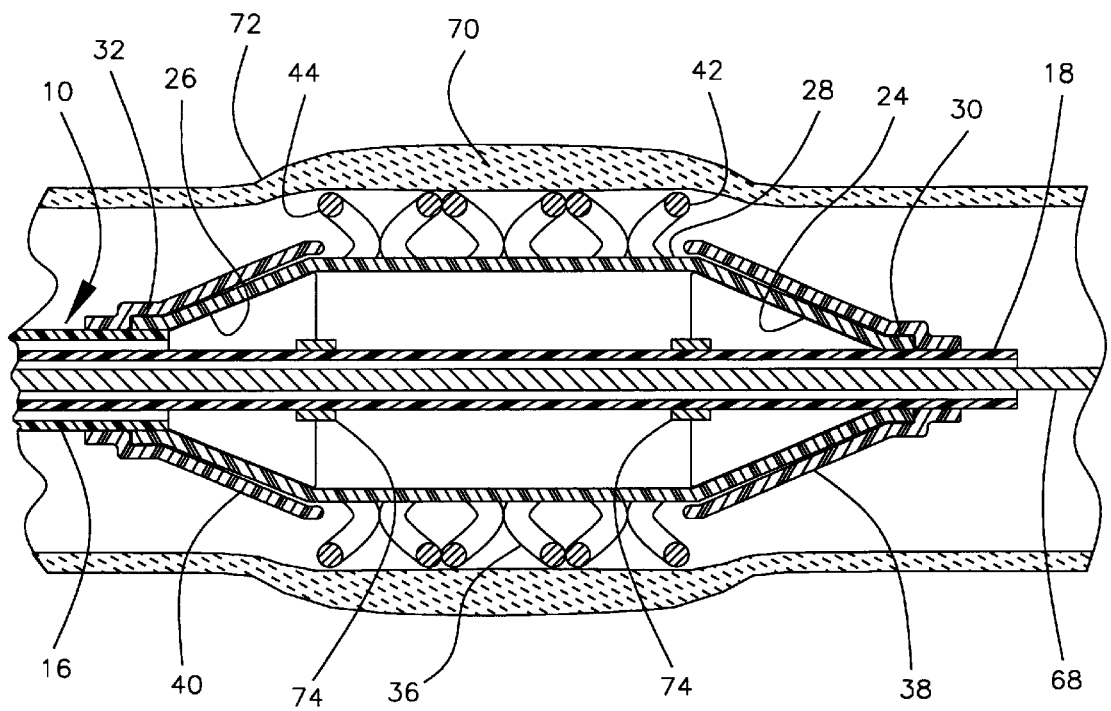
FIG. 7
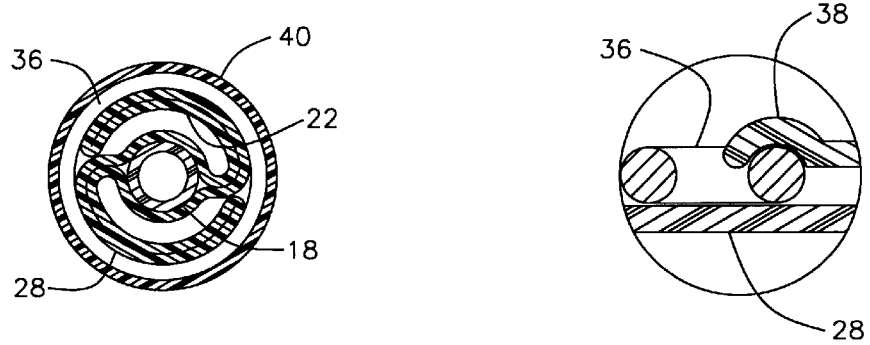
FIG. 3                    FIG. 4

STENT DELIVERY CATHETER AND METHOD OF MAKING SAME

FIELD OF THE INVENTION

The present invention pertains to medical catheters which can be used to deliver a stent to a deployment site within the vascular system of a patient. More specifically, for stent delivery within the cardiovascular system of a patient.

BACKGROUND OF THE INVENTION

Stents are devices deployed in the cardiovascular system of a patient to maintain the patency of a vessel at the site of a lesion, or stenosis. Typically, this requires advancement of the stent through the cardiovascular system and then deployment of the stent at a stenosis site in the vessel. A balloon expandable stent is delivered by securing it onto a balloon of a delivery catheter which then may be advanced through the vascular system to the stenosis site. Once at the stenosis site, the balloon is inflated to deploy the stent.

Significantly, the delivery catheter must bend in different directions as it follows one of the tortuous routes through the vascular system to the stenosis site. As the catheter bends, the attached stent will also bend, and the ends of the stent may deform and flare outwardly from the balloon, thereby increasing the profile of the stent. With such an increased profile the stent may not advance further through the cardiovascular system to cross the lesion site, or the stent may not be easily withdrawn from the body, if that is desired. It is preferred that the stent be retained snugly against the balloon until the stenosis site is reached. Once the stent is placed across the stenosis, the stent should quickly and easily separate from the catheter after the balloon inflates during the deployment of the stent.

Various devices have been proposed to retain the stent against the balloon of a delivery catheter. Several prior art retention devices incorporate pairs of elastic cuffs, or caps, which are placed over the stent proximal and distal ends to retain the ends against the catheter. For these devices, the ends of the stent must slide out from under the end caps as the balloon expands the diameter of the stent. However, the stent may fail to completely exit from within a cap during deployment, possibly leaving the cap caught between the stent and the vessel wall after the balloon has been deflated. To avoid this problem, the end caps may be mounted with only a short overlap of the stent ends, which can lead to premature uncovering of the stent ends and concomitant loss of retention.

In another prior art device, retention sleeves self-retract from their positions overlying the ends of the stent during inflation of a balloon. The sleeves are anchored to a catheter shaft, and they need to fold or accordion to reduce their overall length while sliding down the cones of the expanding balloon. In another prior art example, the ends of a balloon-mounted stent are overlaid by cuffs formed from excess material of the balloon.

It is an object of the present invention to provide a balloon catheter for delivering a stent which retains the stent snugly against the catheter balloon during its advancement into the vascular system.

SUMMARY OF THE INVENTION

The delivery catheter of the present invention includes an elongate shaft and an inflatable tubular balloon that is bonded to the distal end of the catheter shaft. With the balloon deflated, a cylindrical stent is crimped onto the balloon, and proximal and distal end caps are provided to retain the stent on the balloon until it is deployed. The balloon is mounted on the catheter shaft such that excess balloon material can be gathered, or folded, beyond the ends of the stent beneath the end caps. During inflation of the balloon, the excess balloon material unfolds, allowing the balloon to elongate. The portion of the shaft that extends within the balloon is axially stretchable, either elastically or plastically, to accommodate the lengthening of the balloon. The proximal and distal end caps are anchored to the catheter shaft such that the lengthening of the balloon and the shaft portion during inflation will cause the caps to axially separate with the ends of the balloon, thus uncovering the ends of the stent. The invention features a reliable mechanism to withdraw the retention caps from the ends of the stent during deployment, such that the caps of the present invention can cover wider margins at the ends of the stent than were previously advisable, thus providing more dependable retention of the stent on the catheter.

The balloon of the invention is stretch blow-molded from a high-strength thermoplastic material, as is well known in the art of balloons used for dilatation and/or stent delivery. The proximal and distal caps are made of a soft elastic material, preferably a thermoplastic elastomer, which can be heat treated to enhance the ability of the caps to retain the stent against the balloon. The heat treating process for the end caps can be performed using conventional heat-shrink tubing to set the shape of the caps and to partially embed portions of the caps into the distal and proximal margins at the ends of the stent. End caps thus molded establish a firm grip on the stent margins. Heat treating the end caps can also reduce the profile of the assembly to facilitate advancement of the delivery catheter through the cardiovascular system of a patient.

In use of the present invention, the catheter is advanced through the cardiovascular system of a patient until the stent at the distal end of the catheter is positioned across the target lesion. Next, the balloon is inflated to simultaneously expand the stent and to retract the end caps from their positions covering the ends of the stent. With the stent expanded and compressed against the vessel wall, the balloon is deflated to contract it and separate it from the stent. The elastic proximal and distal caps contract with the deflating balloon and will surround the ends of the balloon, when collapsed. If the shaft portion within the balloon has undergone elastic elongation, the balloon will substantially return to its former longitudinally compressed configuration with excess portions. Alternatively, if the distal shaft has undergone plastic deformation during elongation, the balloon will merely collapse onto the catheter shaft. In either event, the delivery catheter, with its reduced deflated balloon profile, can be withdrawn from the patient while the stent remains deployed in the patient's vessel.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 3 is a transverse cross section along lines 3—3 of FIG. 2, showing the assembly in nearly completely collapsed configuration;

FIG. 4 is an enlargement of detail 4 of FIG. 2, showing a retention cap partially embedded into the stent;

FIG. 7 is a longitudinal cross section of the catheter with the stent deployed, and with the balloon partially deflated for withdrawal of the catheter from the blood vessel.

DESCRIPTION OF THE PREFERRED EMBODIMENT

Figure 1:
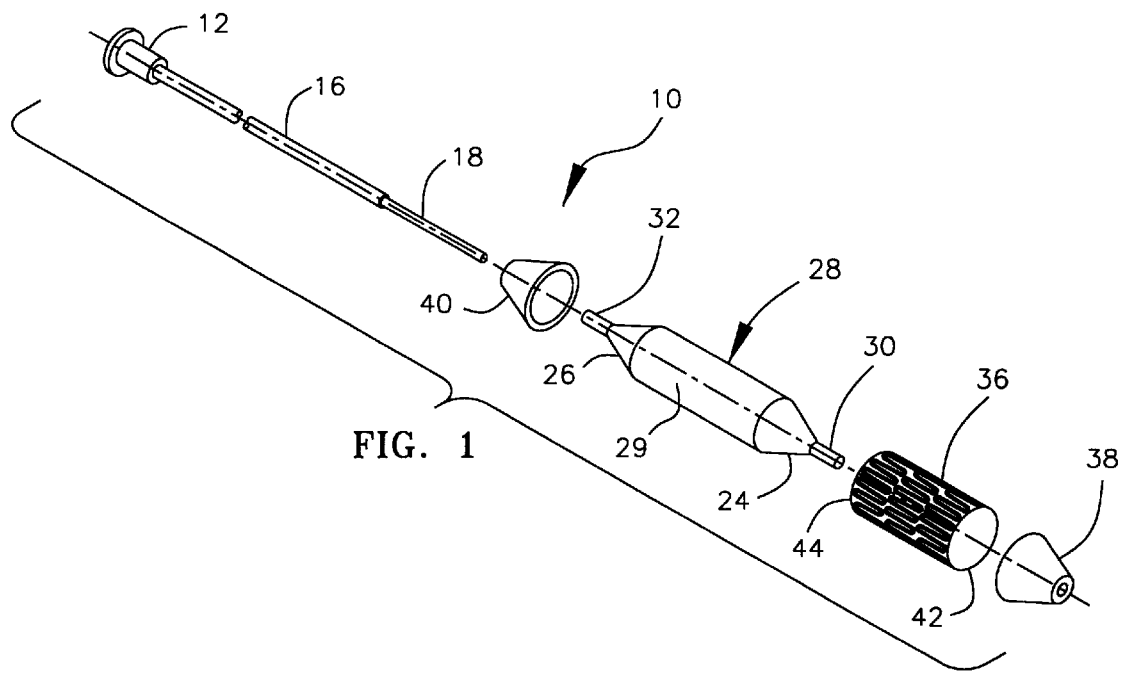
FIG. 1 is an exploded perspective view of the delivery catheter of the present invention and a stent, showing the interconnective relationships between the component parts.

Applicant's invention is advantageous with any expandable cylindrical stent, such as those stents designed for delivery by a tubular balloon. FIG. 1 shows an exploded view of stent delivery catheter 10 in accordance with the present invention. Catheter 10 includes luer fitting 12 which is attached in fluid communication with proximal shaft 16. Distal shaft 18 is preferably the inner tube of a coaxial catheter design, as depicted in FIG. 1, wherein distal shaft 18 extends through proximal shaft 16, creating an annular inflation lumen therebetween. In an alternative design, not shown, distal shaft 18 is a single lumen extension of a multi lumen proximal shaft, the two shaft portions being joined adjacent or proximal to the balloon proximal neck 32. Either a multi lumen extrusion or a coaxial assembly may be used to construct either over-the-wire type catheters or rapid exchange type catheters. The features of the invention may also be designed into a fixed-wire balloon catheter wherein distal shaft 18 would surround a guidewire that is integral to the catheter assembly. In all cases, distal shaft 18 extends distally of proximal shaft 16. All of the shaft designs mentioned above are well known to artisans in the field of cardiovascular catheters.

Balloon 28 has a generally cylindrical body 29 for receiving a stent and thus deploying it to a cylindrical shape, and distal and proximal cones 24, 26, which taper respectively to distal and proximal bands, or necks 30, 32. Balloon 28 is mounted adjacent the distal end of catheter 10, surrounding distal shaft 18 in such a way that excess, or slack, balloon material is generated, as will be further explained below. Balloon distal neck 30 is fixed to distal shaft 18, and balloon proximal neck 32 is fixed to, or alternatively may be an integral extension of, proximal shaft 16. The preferred method of attaching balloon necks 30, 32 to respective shafts 18, 16 is by thermal, or melt, bonding, although suitable adhesive maybe used. The balloon of the invention is stretch blow-molded from a high-strength, biocompatible, thermoplastic material, as is well known in the art of balloons for dilatation and/or stent delivery. In the preferred embodiment of the invention, the balloon is made of a thermoplastic elastomer, such as PEBAX®, a polyether block amide from Elf Atochem North America, Inc., Philadelphia, Pa.

Before stent 36 is crimped onto body 29 of balloon 28, the balloon is deflated, forming wings that are wrapped around distal shaft 18, as shown in FIG. 3. Distal cap 38 and proximal cap 40 span, respectively, distal and proximal cones 24, 26, and lie over, respectively, distal stent end 42 and proximal stent end 44 to retain stent 36 against balloon 28. Specifically, distal cap 38 is fixed to distal shaft 18 on or adjacent distal balloon neck 30 and extends proximally from neck 30 to span distal balloon cone 24 to envelop stent distal end 42. Similarly, proximal cap 40 is fixed to proximal shaft 16 on or adjacent proximal balloon neck 32 and extends distally from neck 32 to span proximal balloon cone 26 to envelop stent proximal end 44. Preferably, caps 38, 40 are fastened to their respective points of attachment by thermal, or melt, bonding, although suitable adhesive may be used. For this purpose, proximal shaft 16, distal shaft 18, balloon 28 and caps 38, 40 are all preferably made of thermally bonded, or melt compatible materials. The distal and proximal caps 38, 40 are preferably made of a low durometer (40A–50A) thermoplastic polyurethane, such as Tecoflex™ by Thermo-Electron, Inc., Waltham, Mass. Alternative materials for caps 38, 40 are low durometer grades of PEBAX®, such as 2533 or 3533. Thin walled silicone tubing can also be used for caps 38, 40, although fastening such non thermoplastic materials would require an adhesive.

Figure 2:
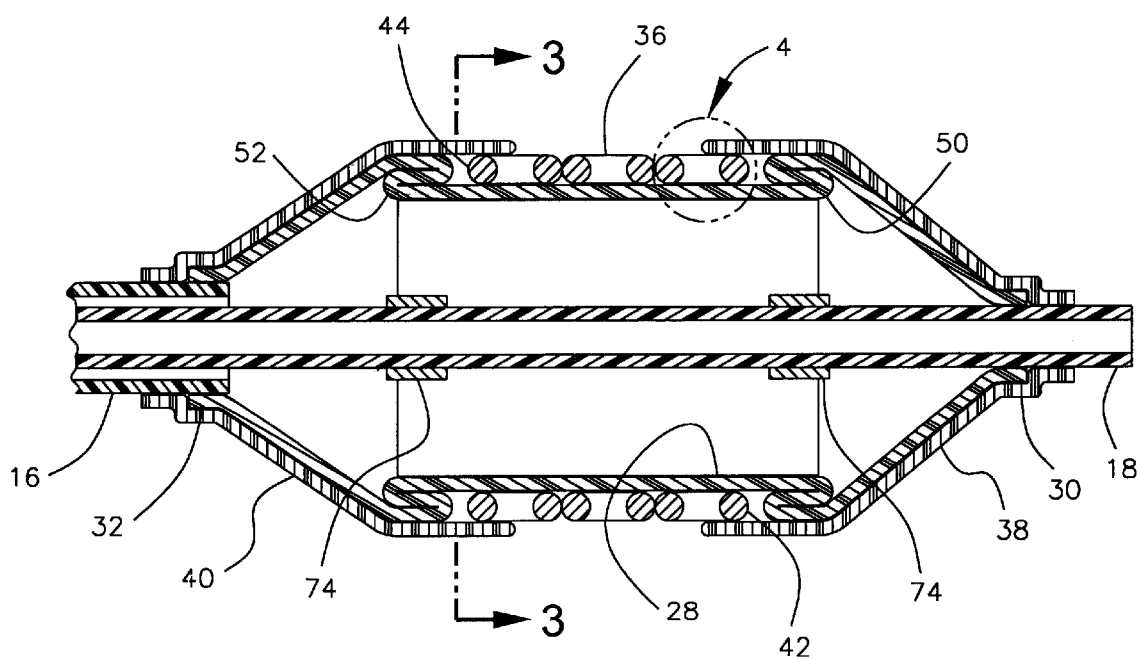
FIG. 2 is a longitudinal cross section of the distal end of the assembled catheter, shown partially inflated.

FIG. 2 shows the distal end of the catheter and stent assembly of the invention in a slightly expanded configuration for clarity, whereas during advancement through the vasculature, balloon 28, stent 36 and end caps 38, 40 would be fitted snugly around distal shaft 18 to give the assembly a low crossing profile. Balloon 28 is attached to catheter 10 with a mounted balloon length that is shorter than the as-molded, or formed, balloon length to create slack, or excess balloon material. Preferably, cylindrical body 29 is longer than stent 36 such that the excess material is generated in proximal and distal portions of the body material. Although the excess can be formed in any portion of body 29, or in any combination of body 29 and/or cones 24, 26, the material of body 29 is generally thinner than the material of cones 24, 26. Therefore, it is preferred to induce the excess in the most proximal and distal portions of body 29 adjacent cones 24, 26. Thinner excess material is easier to fold, and the folds thus formed have better flexibility and lower profile than is achievable with thicker material.

The excess material in balloon 28 is preferably gathered and formed into distal and proximal circumferential folds 50, 52 near respective distal and proximal ends 42, 44 of stent 36. Although distal and proximal folds 50, 52 are shown in the preferred configuration wherein single folds lie respectively towards stent distal and proximal ends 42, 44, the excess balloon material can be folded away from stent 36, and/or multiple folds can be created. Any gathered or folded configuration of the excess balloon material will work in the invention, although it is preferred to avoid forming wrinkles in the body portion that lies within stent 36. Such wrinkles could increase the crossing profile of the assembly 29 and, as balloon 28 elongates during inflation, unfurling of wrinkles within stent 36 could apply longitudinal tension to the stent, which may be undesirable for many stent designs.

Figure 8:
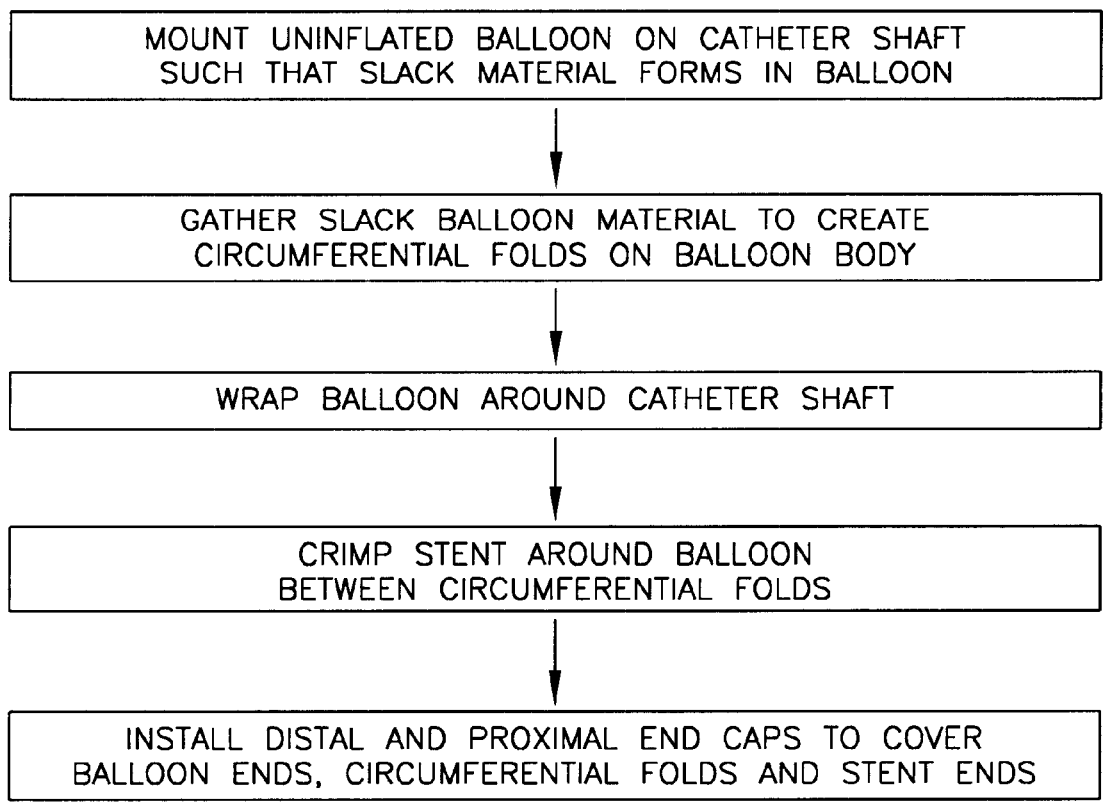
FIG. 8 is a flow chart depicting a method of making the stent delivery catheter of the present invention.

As shown in FIG. 8, the assembly steps for the invention preferably include:

a) mounting balloon 28 onto catheter 10 such that excess material is formed in balloon 28;

b) gathering the excess balloon material to create distal and proximal circumferential folds 50, 52 at the proximal and distal ends of cylindrical body 29;

c) deflating balloon 28 and wrapping wings 22 thus formed around distal shaft 18;

d) crimping stent 36 over balloon 28 between folds 50, 52;

e) installing distal and proximal end caps 38, 40 over respective distal and proximal balloon cones 24, 26, over respective distal and proximal circumferential folds 50, 52, and over respective distal and proximal stent ends 42, 44.

Caps 38, 40 may be bonded to the catheter shaft beyond balloon ends 30, 32. Alternatively caps 38, 40 may be bonded to the balloon necks that are bonded to the shaft. After installation of end caps 38, 40, conventional heat shrink tubing is preferably used to heat treat caps 38, 40, setting a compressed shape therein and partially embedding into stent 36 the cap ends that lie over stent ends 42, 44, as shown in FIG. 4. In addition to establishing an engagement between caps 38, 40 and stent 36, the heat set process also reduces the overall profile of catheter 10 at stent 36. Thermally setting distal and proximal end caps 38, 40 such that they become embedded in or envelop distal and proximal ends 42, 44.

The heat shrink tubing used is selected to be effective at temperatures that will heat set the material of end caps 38, 40 without altering the physical properties of biaxially oriented balloon 28. Suitable shrink tubing can be made of standard or irradiated polyethylene tubing that has been thermally expanded into a capture tube, then cooled. Alternatively, a variety of pre-expanded polyolefin shrink tubing is available from sources such as Raychem Corp., Menlo Park, Calif. After placing a length of selected shrink tubing over the distal end of the assembly comprising catheter 10, the application of hot air at the appropriate temperature causes the tubing to radially compress the assembly while conducted heat thermally sets the material of caps 38, 40. During this heat setting step, the lumen of distal shaft 18 is preferably supported by a stainless steel wire mandrel.

Figure 5:
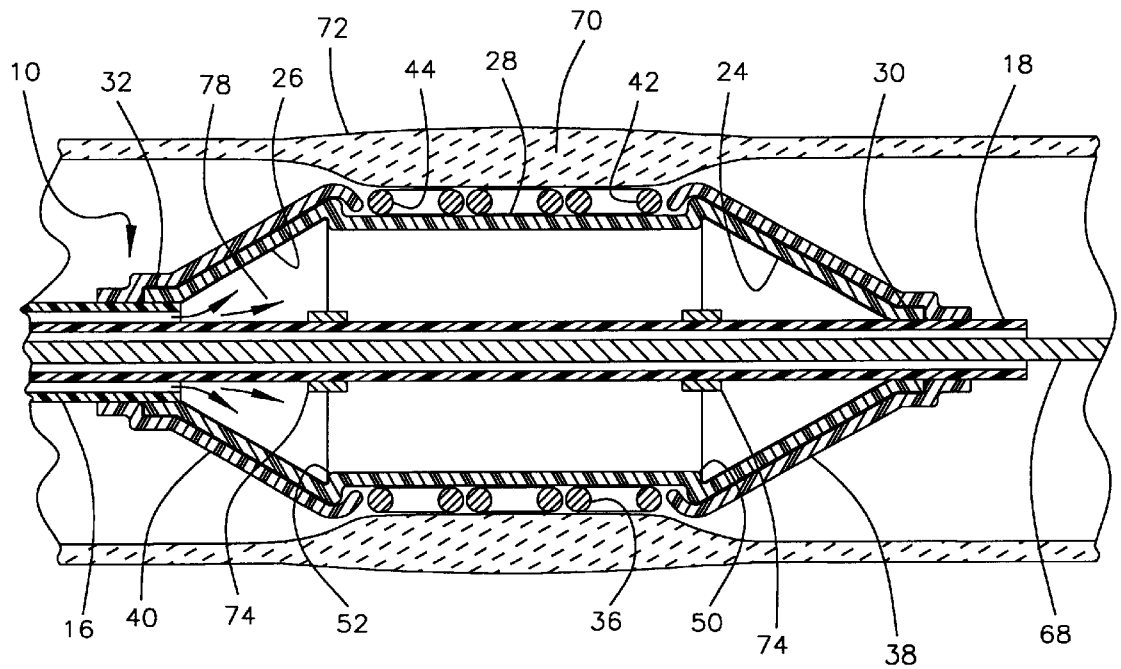
FIG. 5 is a longitudinal cross section of the catheter with the stent placed within a stenosis of a blood vessel and with the balloon partially inflated for deployment of the stent.

In the operation of delivery catheter 10 of the present invention, and referring now to FIG. 5, catheter 10 is advanced along guidewire 68 to stenosis 70 in blood vessel 72. Once stent 36 is across stenosis 70, as determined by one or more radiopaque marker bands 74 inside balloon 28, the balloon is inflated. An inflation device (not shown) forces dilute radiopaque contrast media through an inflation lumen in proximal shaft 16 into the interior of balloon 28, as indicated by arrows 78. As pressure increases in balloon 28, distal and proximal cones 24, 26 of balloon 28 begin to expand from their deflated, wrapped configuration. Caps 38, 40 also expand conically, driven by underlying cones 24, 26, effecting a partial withdrawal of the caps from the margins of stent 36.

The hydraulic pressure in balloon 28 also forces balloon 28 to elongate significantly, which is permitted by the unfurling of circumferential folds 50, 52. Elongation of balloon 28 forces balloon necks 30, 32 apart, causing shaft 18 to lengthen under the tension created in distal shaft 18 within balloon 28. The deformation of shaft 18 may be either plastic or elastic, depending on the material selected for shaft 18. The preferred material for shaft 18 is a polymer that can be bonded thermally and that will deform plastically, such as PEBAX®. Alternative materials for shaft 18 are polyamides, such as VESTAMID® nylon 12, by Creanova, Somerset, N.J., or high or low density polyethylenes (HDPE, LDPE). Alternatively, catheter 10 can be constructed as a coaxial catheter according to U.S. Pat. No. 6,066,157, such that elongation of balloon 28 causes distal shaft 18 to move distally relative to proximal shaft 16. In such a telescoping shaft design, the entire length of distal shaft 18, which may extend the full length of the catheter, is available to absorb the tension applied by balloon 28. In the present invention, the lengthening of shaft 18 drives apart end caps 38, 40, ensuring that stent ends 42, 44 are completely uncovered such that caps 38, 40 cannot get trapped between stent 36 and blood vessel 72 during deployment of stent 36.

The relative timing of the expansion of cones 24, 26 and the elongation of balloon 28 depends, in part, on the expansion properties of stent 36. For example, if expansion of stent 36 requires relatively high inflation pressure, balloon 28 may elongate, accompanied by the unfurling of circumferential folds 50, 52 before stent 36 is expanded. Alternatively, if stent 36 can be distended at lower inflation pressures, balloon 28 may elongate after stent 36 has been expanded. It is also possible for balloon expansion and elongation to take place simultaneously. The tensile properties of shaft 18 also affect how much inflation pressure is required to elongate balloon 28.

Figure 6:
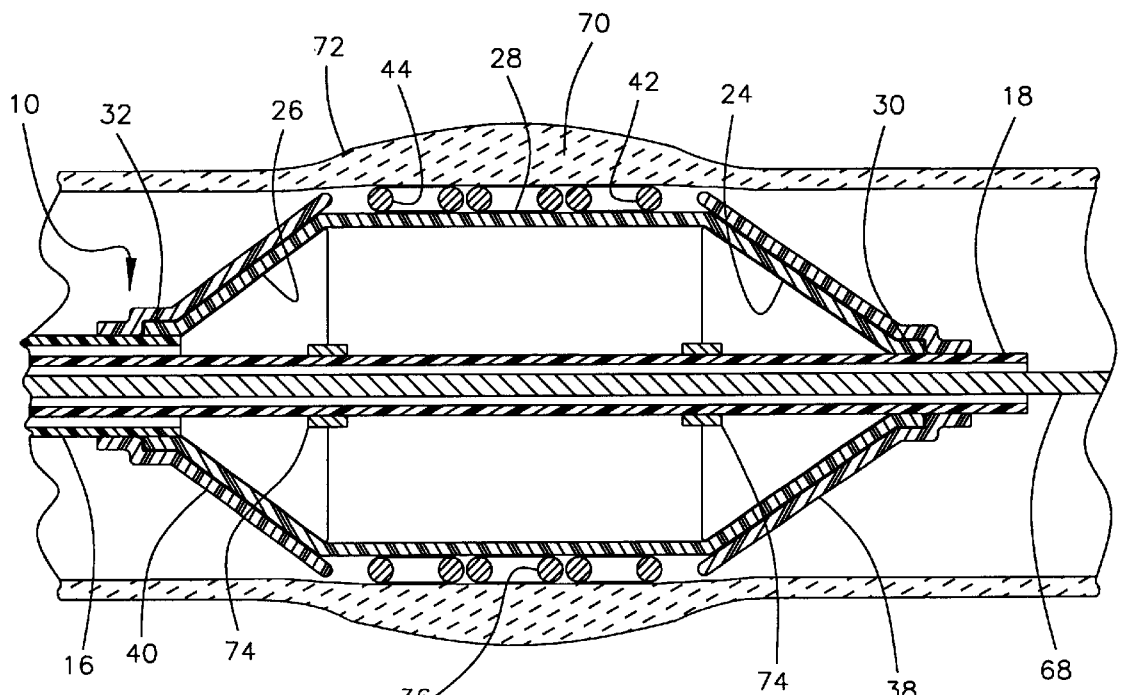
FIG. 6 is a longitudinal cross section of the catheter with the stent fully expanded against the blood vessel when the balloon is fully inflated.

FIG. 6 shows balloon 28 in a fully inflated state with circumferential folds 50, 52 having been unfurled In this configuration, the portion of distal shaft 18 within balloon 28 has extended to accommodate the lengthening of balloon 28. Further, caps 38, 40 have slid completely off of respective stent ends 42, 44, with the caps now lying firmly against respective balloon cones 24, 26. Stent 36 is fully expanded and has been deployed against dilated blood vessel 72. Following deployment of stent 36, catheter 10 is ready to be deflated to facilitate removal from the patient.

FIG. 7 shows balloon 28, which has been partially deflated, by withdrawing inflation media through the inflation lumen in proximal shaft 16, to contract and separate the balloon from expanded stent 36. When deflation is complete, balloon 28 will snugly adhere to distal shaft 18, which preferably remains at its stretched length. In an alternative embodiment described above, the deformation of distal shaft 18 may be elastic, in which case shaft 18 contracts to substantially its original length upon deflation of balloon 28, thus re-generating excess material in balloon 28. As balloon 28 contracts, proximal and distal caps 38, 40 contract elastically toward their original heat set shapes, thus aiding balloon cones 24, 26 and wings 22 of deflating balloon 28 to at least partially re-wrap around distal shaft 18. Thus, the resilient qualities of proximal and distal caps 38, 40 enhance the ability of assembled catheter 10 to disengage from deployed stent 36 by reducing the profile of balloon 28. Expanded stent 36 remains permanently deployed against blood vessel 72. Once separated from stent 36, delivery catheter 10 is withdrawn from the patient's vascular system. It is to be understood that the particular stent delivery balloon catheter and method for manufacturing thereof are merely illustrative of the presently preferred embodiments of the invention and that no limitations are intended to the details of construction or design herein shown other than as described in the appended claims.

What is claimed is:

1. A stent delivery catheter comprising:
    a catheter shaft having an inflation lumen there through and a longitudinally extendable portion at a distal end thereof;
    an inflatable tubular balloon having first and second ends and a formed length, the balloon being mounted and wrapped around the catheter shaft surrounding the extendable portion thereof and being in communication with the inflation lumen, the balloon having a mounted length that is shorter than the formed length such that excess balloon material forms at least one circumferential fold in the balloon;
    a balloon expandable stent having open ends, the stent being crimped about the balloon between the ends thereof; and an elastic retention cap, the cap being fixed to the shaft adjacent the first end of the balloon, the cap extending over the first end of the balloon such that the cap lies over the stent end nearest the first end of the balloon.

2. The catheter of claim 1 wherein the balloon is inflatable from a first configuration wherein the cap lies over one end of the stent, to a second configuration wherein the at least one circumferential fold of the balloon is unfolded, the cap is longitudinally separated from the stent and the stent is expanded for deployment in a vessel of a patient.

3. The catheter of claim 2 wherein the balloon is deflatable from the second configuration to a third configuration wherein the balloon is substantially collapsed around the extendable portion of the catheter shaft, the cap lies substantially snugly about the first end of the balloon, and the balloon is separated from the expanded stent to allow removal of the catheter from the vessel while the expanded stent remains deployed in the vessel.

4. The catheter of claim 2 wherein the extendable portion of the catheter shaft has a first length corresponding to the first configuration of the balloon and the extendable portion has a second length corresponding to the second configuration of the balloon, the second length being longer than the first length.

5. The catheter of claim 4 wherein the extendable portion of the catheter shaft comprises a material that permits elongation thereof from the first length to the second length.

6. The catheter of claim 5 wherein the shaft material is a thermoplastic elastomer.

7. The catheter of claim 6 wherein the thermoplastic elastomer is a polyether block amide co-polymer.

8. The catheter of claim 1 wherein the retention cap is composed of an elastic material.

9. The catheter of claim 8 wherein the elastic material is a low durometer synthetic rubber.

10. The catheter of claim 1 wherein the retention cap end that lies over one end of the stent is partially embedded into the stent.

11. The catheter of claim 1 wherein the retention cap is fixed to a neck at the first end of the balloon, the neck being fixed to the shaft.

12. A stent delivery catheter comprising:
- a catheter shaft having an inflation lumen there through and a longitudinally extendable portion at a distal end thereof;
- an inflatable tubular balloon having proximal and distal ends and a formed length, the balloon being mounted and wrapped around the catheter shaft surrounding the extendable portion thereof and being in communication with the inflation lumen, the balloon having a mounted length that is shorter than the formed length such that excess balloon material forms at least one circumferential fold;
- an expandable stent having proximal and distal ends, the stent being crimped about the balloon;
- a distal elastic retention cap, the distal cap being fixed to the shaft adjacent the distal end of the balloon, the distal cap extending over the distal end of the balloon and the distal end of the stent; and
- a proximal elastic retention cap, the proximal cap being fixed to the shaft adjacent the proximal end of the balloon, the proximal cap extending over the proximal end of the balloon and the proximal end of the stent.

13. The catheter of claim 12 wherein the at least one circumferential fold comprises a distal circumferential fold formed distal to the distal end of the stent and a proximal circumferential fold formed proximal to the proximal end of the stent.

14. The catheter of claim 13 wherein the distal and proximal caps cover respectively the distal and proximal circumferential folds.

15. The catheter of claim 14 wherein the catheter is transformable between a first configuration wherein the balloon is deflated and the distal and proximal caps lie respectively over the distal and proximal ends of the stent, and a second configuration wherein the balloon is inflated, the distal and proximal circumferential folds of the balloon are unfolded, the caps are longitudinally separated from the stent and the stent is expanded for deployment in a vessel of a patient.

16. The catheter of claim 15 wherein the catheter is transformable from the second configuration to a third configuration wherein the balloon is substantially collapsed around the catheter shaft, the distal and proximal caps lie substantially snugly about the ends of the balloon and the balloon is separated from the expanded stent.

17. A method of deploying a stent in the vessel of a patient, comprising the steps of:
(a) providing an elongate, flexible catheter having a deformable inner shaft positioned within a lumen of an outer shaft to extend distally therefrom, further providing an inflatable tubular balloon, the balloon having proximal and distal ends and having proximal and distal circumferential folds and having a stent crimped thereon between the proximal and distal folds, the balloon distal end being bonded to the inner shaft and the balloon proximal end being bonded to the outer shaft, the balloon having a proximal cap bonded to the outer shaft adjacent the balloon proximal end and extending distally therefrom to cover the balloon proximal fold and to lie over the stent proximal end, the balloon having a distal cap bonded to the inner shaft adjacent the balloon distal end and extending proximally therefrom to cover the balloon distal fold and to lie over the stent distal end;
(b) positioning the balloon within a stenosis in a blood vessel of a patient;
(c) inflating the balloon from a first configuration, wherein the caps secure the stent to the balloon, to a second configuration, wherein the folds of the balloon unfold to longitudinally release the caps off of the stent, wherein the inner shaft elongates to accommodate the unfolding of the folds and wherein the stent has expanded against the blood vessel;
(d) deflating the balloon from the second configuration to a third configuration, wherein the balloon separates from the expanded stent and wherein the caps lie substantially against the balloon; and
(e) withdrawing the catheter from the vessel.

* * * * *